United States Patent [19]

Poirier et al.

[11] Patent Number: 5,454,842
[45] Date of Patent: Oct. 3, 1995

[54] CETANE IMPROVER COMPOSITIONS COMPRISING NITRATED FATTY ACID DERIVATIVES

[75] Inventors: Marc-Andre Poirier; David E. Steere, both of Sarnia, Canada; James A. Krogh, Jamesville, Wis.

[73] Assignee: Exxon Research & Engineering Co., Florham Park, N.J.

[21] Appl. No.: 348,528

[22] Filed: Dec. 2, 1994

[51] Int. Cl.⁶ ........................................... C10L 1/22
[52] U.S. Cl. ..................... 044/324; 44/323; 558/480; 558/483
[58] Field of Search ................... 44/323, 324; 558/480, 558/483

[56] References Cited

U.S. PATENT DOCUMENTS

| | | | |
|---|---|---|---|
| 3,324,168 | 6/1967 | Müller et al. | 558/483 |
| 4,330,304 | 5/1982 | Gorman | 44/63 |
| 4,365,973 | 12/1982 | Irish | 44/56 |
| 4,448,587 | 5/1984 | Hinkamp et al. | 44/324 |
| 4,473,378 | 9/1984 | Hanlon et al. | 44/324 |
| 4,536,190 | 8/1985 | Seemuth et al. | 44/57 |
| 4,549,883 | 10/1985 | Purcell et al. | 44/324 |
| 4,585,461 | 4/1986 | Gorman | 44/53 |
| 4,992,605 | 2/1991 | Craig et al. | 585/240 |
| 5,114,433 | 5/1992 | Dubreux et al. | 44/322 |
| 5,258,049 | 11/1993 | Liotta Jr. et al | 44/324 |

FOREIGN PATENT DOCUMENTS

| | | |
|---|---|---|
| 157684 | 10/1985 | European Pat. Off. . |
| 293069 | 11/1988 | European Pat. Off. . |
| 467628 | 1/1992 | European Pat. Off. . |
| 537931 | 4/1993 | European Pat. Off. . |
| 2227752 | 10/1985 | United Kingdom . |
| 2227751 | 8/1990 | United Kingdom . |
| 9308244 | 4/1993 | WIPO . |

OTHER PUBLICATIONS

"How Do Diesel Fuel Ignition Improvers Work", Clothier et al Chem Soc Rev 1993, pp. 101–108, (month unknown).

"Tall Oils" Kirk–Othmer Encyclopedia of Chemical Technology 2nd Edition vol. 19, 1969, (month unknown).

"Rhenium and Its Compounds as Hydrogenation Catalysts III Rhenium Heptoxide" Broadbent et al, J. Org Chem 24 1847 (Jun. 1959).

"Substituent Effects on Hydrogenation of Aromatic Rings: Hydrogenation vs Hydrogenalysis in Cyclic Analogues of Benzyl Ethers" Anzalone et al., J. Org. Chem 50 2128, 1985 (month unkown).

"Quaternary Ammonium Nitrates, Part I, Preparation from Alkyl Nitrates and from aw Polymethylene Dinitrates" Lane J. Chem Soc 1953, p. 1172 (month unknown).

*Primary Examiner*—Ellen M. McAvoy
*Attorney, Agent, or Firm*—Joseph J. Allocca

[57] ABSTRACT

The present invention is directed to materials which improve the cetane number of diesel fusel when added in an amount in the range of 0.01 to 2 wt % to such fuel. The materials are the nitration product of alcohols obtained by the reduction of tall oil fatty acids, tall oil fatty acid esters, vegetable oils and mixtures thereof.

5 Claims, No Drawings

CETANE IMPROVER COMPOSITIONS COMPRISING NITRATED FATTY ACID DERIVATIVES

BACKGROUND OF THE INVENTION

1. Field of the Invention

This invention relates to diesel fuel or other middle distillate fraction, excluding jet, cetane improvement additives.

2. Description of Related Art

Fuel ignition in diesel engines is achieved through the heat generated by air compression, as a piston in the cylinder moves to reduce the cylinder volume during the compression stroke. In the engine, the air is first compressed, then the fuel is injected into the cylinder; as the fuel contacts the heated air, it vaporizes and finally begins to burn as the self-ignition temperature is reached. Additional fuel is injected during the compression stroke and the fuel burns almost instantaneously, once the initial flame has been established. Thus, a period of time elapses between the beginning of fuel injection and the appearance of a flame in the cylinder. This period is commonly called "ignition delay" and must be relatively short in order to avoid "diesel knock". A major contributing factor to diesel fuel performance and the avoidance of "diesel knock" is the cetane number of the diesel fuel. Diesel fuels of higher cetane number exhibit a shorter ignition delay than do diesel fuels of a lower cetane number. Therefore, higher cetane number diesel fuels are desirable to avoid diesel knock. Most diesel fuels possess cetane numbers in the range of about 40 to 55 and a sulfur content of about 500 ppm and less. A good correlation between ignition delay and cetane number has been reported in "How Do Diesel Fuel Ignition Improvers Work" Clothier, et al., Chem. Soc. Rev, 1993, pg. 101–108 in the region 3<t igni<8 m sec using the equation CN=91–6.4 t igni, which reflects contributions by engine timing and levels of additives in the fuels. Correcting the equation to remove the influences of timing and additives results in the equation CN=85–6.0 t igni.

Cetane improvers have been used for many years to improve the ignition quality of diesel fuels. The use of cetane improvers is increasing due to the increased demand for diesel fuel which has resulted in a widening of the fraction recovered, the so called middle distillate fraction, and the lowering of the natural cetane number of diesel base stocks caused by more severe refining of crude oil and the effort made to produce low emission diesel.

Many types of additives have been prepared and evaluated to raise the cetane number of diesel fuel. Such additives include peroxides, nitrates, nitrites, azo compounds and the like.

Alkyl nitrates such as amyl nitrate, hexyl nitrate and mixed octyl nitrates have been used commercially with good results. Other nitrates such as 2-methyl-2-nitropropyl nitrate (U.S. Pat. No. 4,536,190) have been suggested as cetane improvers but were found to be shock sensitive. However, it is generally accepted that organic nitrates, more specifically the commercial 2-ethylhexyl nitrate, are the most cost-effective additives to improve cetane number of diesels. Because of its relatively low cost, and environmentally friendly nature (ashless), there has been limited work done in this area to replace the 2-ethylhexyl nitrate.

U.S. Pat. No. 4,992,605 discloses a process for producing high cetane hydrocarbons in the diesel boiling range, by hydroprocessing tall oil or vegetable oils such as canola, sunflower, soybean and rapeseed oil at temperatures in the range from 350° C. to 450° C. and pressures of 4.8 to 15.2 MPa. The hydrocarbons mixture produced by this process has a relatively high cetane number (50–85 CN), however, relatively high concentrations (10–15%) are required to increase the cetane number of the diesel fuel by about 3 to 5 cetane numbers. Moreover, because of the waxy nature of the material, it has a relatively high cloud point (4°–16° C.) which limits its usefulness to blending into summer diesel.

U.S. Pat. No. 4,585,461 refers to a method of manufacturing a cetane improver from fusel oil, a waste product from the distillation of alcoholic beverages. Fusel oil provides a cheap source of ethyl alcohol (5 to 25%), isobutyl alcohol (16 to 33%) and isoamyl alcohol (30 to 77%). However, it is mentioned that fusel oil is foul smelling, quite toxic and one of its constituent alcohols is a teratogen. Moreover, lower molecular weight nitrate such as ethyl nitrate or amyl nitrate tend to be explosive in inverse proportion to their molecular weight. Such materials are hazardous if their molecular weight is 76, but become less hazardous as their weight reaches 174. "Fusel" nitrate has a molecular weight of 119 and is moderately hazardous.

Organic nitrates and organic peroxides are well known to cause substantial increases in cetane number of diesel fuels. It is generally accepted that organic nitrates, more specifically the commercial 2-ethylhexyl nitrate (DII-3 sold by Ethyl Petroleum Additives), are the most cost-effective additives to improve the cetane number of diesel fuels.

W093/08244 discloses cetane improving additives comprising 13–25 carbon alkyl nitrates. The nitrates are obtained by nitration of oxo process alcohols. The fuel contains, in addition to the alkyl nitrate, an ashless dispersant, preferably a macrocyclic polyamine dispersant.

EP157,684 discloses nitrates of alkyoxylated alcohol or phenol added to diesel fuels to improve cetane index and keep fuel injector systems clean by detergent action. The organic nitrate is of the formula

wherein R is a $C_6$ to $C_{20}$ alkoxy or aryl substituted by a $C_4$–$C_{18}$ alkyl chain, X is hydrogen or methyl and n is 1 to 15, R is a radical derived from an aliphatic monoalcohol of natural or synthetic origin such as hexanol, octanol myristyl or stearyl alcohol or alcohols from the oxo-process.

G.B. Patent 2,227,752A teaches that cetane number of a hydrocarbon-based fuel is increased by the addition of a minor amount of a parketal of the formula $R_2R_3C(OOR_1)_2$ wherein $R_1$ is a $C_4$–$C_{10}$ tertiary alkyl group and $R_2$ and $R_3$ together with the attached C atom form a cycloalkane ring optionally substituted by one or more $C_1$–$C_4$ alkyl radicals or other essentially inert substituents. The perketal is not used in combination with an alkyl nitrate.

Patent EP0537931 discloses a fuel composition for reducing emissions on combustion consisting of a middle distillate fuel, organic nitrate combustion improver and a tert-alkyl peroxyalkanoate or peroxybenzoate.

U.S. Pat. No. 5,114,433 describes a process for improving the cetane number of a directly distilled diesel fuel by intimately contacting same with hydrogen peroxide in the presence of carboxylic acid or with a percarboxylic acid in the presence or absence of hydrogen peroxide.

G.B. Patent 2,227,751A discloses a hydrocarbon-based fuel to which has been added a minor amount, sufficient to increase the cetane value of the fuel, of a perester of the formula $R_1COOOR_2$ where $R_1$ is a $C_5$–$C_{20}$ secondary or tertiary alkyl group and $R_2$ is a $C_4$–$C_{10}$ tertiary alkyl group.

U.S. Pat. No. 4,365,973 discloses a middle distillate fuel additive composition to improve cold flow properties, cetane, pour point, wax formation and anti-icing characteristics and comprising a cold flow improver, preferably vinyl acetate-ethylene copolymer, a cetane improver comprising paraffinic nitrate or a mixture of nitrates and an anti-icer comprising an aliphatic alcohol or cyclic aliphatic alcohol having from 1 to 6 carbon atoms.

EP 467,628 discloses a middle distillate composition to reduce atmospheric pollutants (NOx, CO and/or hydrocarbons). the fuels incorporate a peroxy ester combustion improver of the formula $(R-O-O-(CO))_n R^1$ where R and $R^1$ are both hydrocarbyl groups. Suitable peroxy esters include tert-butyl peroxydodecanoate, di-(tert-butyldiperoxy) phthalate and 1,1-dimethylpropylperoxy benzoate. The peroxy ester is used in combination with an organic nitrate ester such as 2-ethylhexyl nitrate.

U.S. Pat. No. 4,330,304 discloses a fuel additive for improving the combustion efficiency of fuels for diesel engines, jet engines, boilers and other apparatus. The additive comprises a hydroperoxide such as cumene hydroperoxide, a nitroparaffin and propylene oxide.

EP 293,069 discloses a cetane improver comprising tetralin hydroperoxide. The cetane improver is produced by partially hydrogenating a naphthalene or alkyl naphthalene-containing hydrocarbon oil to obtain tetralins, which are then partially oxidized to produce a hydrocarbon oil containing tetraline hydroperoxides.

U.S. Pat. No. 5,258,049 discloses a diesel fuel containing the nitric acid ester of 1-phenyl ethanol as cetane improver.

DESCRIPTION OF THE INVENTION

The present invention is directed to a cetane improver composition and to fuels containing such composition.

The cetane improver composition comprises fatty alcohol nitrate esters, preferably tall oil fatty alcohol nitrate esters which are the nitration products of tall oil fatty alcohols, vegetable oil fatty alcohols and mixtures thereof. The alcohols are obtained by the reduction of tall oil fatty acids, tall oil fatty acid esters, vegetable oils and mixtures thereof.

Fatty alcohols secured from tall oil or vegetable oils could be unsaturated or saturated alcohols depending upon the reduction process used to produce them. However, saturated fatty alcohols obtained from tall oil or vegetable oils are most preferred.

Tall oil is a natural product of pine trees and is a by-product of alkaline Kraft wood pulping process. Pine wood chips are digested in aqueous liquor containing sodium hydroxide and sodium sulfide at 170° C. for two hours. This digestion delignifies the wood and produces cellulose pulp, sodium soap of rosin acids, fatty acids and lignin degradation products. Cellulose is stable under these conditions and remains slurried in the black liquor. When the pulping reaction is complete, pulp is separated from the black liquor and washed. the pulp can be used as such or it is bleached or otherwise upgraded.

The black liquor contains valuable inorganic chemicals and must be recovered for economic and environmental reasons. Excess water is evaporated and the curdy soap is containing all tall oil components is salted out and floats to the top. This black liquor soap is skimmed and is acidulated to product water-insoluble crude tall oil. Crude tall oil contains from 40–75% fatty acids, 20–54% rosin acids and 7–12% unsaponifiables. Crude tall oil can be refined by fractional distillation to produce tall oil fatty acids, tall oil rosin, distilled tall oil, tall oil heads and tall oil pitch. Refined tall oil contains 90–99% fatty acids, 0–5% rosin acids and 0.5–3% unsaponifiables. In this invention crude tall oil is the most preferred starting material.

The crude (whole) tall oil, the purified tall oil fatty acids fraction, tall oil fatty acid esters, vegetable oil and mixtures thereof are subjected to reduction, that is catalytic hydrogenation which converts the acid or ester components to fatty alcohols. In the case of vegetable oils such as corn oil, olive oil, canola, sunflower, soybean, rapeseed, coconut and the like which are known to be triglycerides with three fatty acid chains, hydrogenation produces glycerol and fatty alcohols which are separated by aqueous extraction to yield purified fatty alcohols.

The fatty alcohols produced by the reduction (i.e. catalytic hydrogenation) of the tall oil, tall oil fatty acid, tall oil fatty acid esters, vegetable oils and mixtures thereof are nitrated to produce the fatty alcohol nitrate esters which are useful as cetane improvers. Fatty acids, crude tall oil and mixtures thereof can be esterified by the reaction of an alcohol such as methanol in the presence of sulfuric acid at reflux temperature, see J. Org. Chem. 50, 8 (1985), followed by catalytic hydrogenation which converts the esters to fatty alcohols.

"Fatty acids, crude tall oil and mixture thereof can also be esterified by the reaction of a glycol (1 mole to 1 mole) in the presence of sulfuric acid at reflux temperature, see J. Org. Chem. 50, 2128 (1985), followed by nitration of the ester-alcohols which converts the alcohol functionality to nitrate esters. The preferred glycol has the following formula: $HO-(CH_2)_x-X-(CH_2)_xOH$ where x is 1 to 5 and X is $CH_2$, S or O. Most preferably X is $CH_2$ and O. Such compounds include ethylene glycol, 1,3-propanediol, dipropylene glycol and the like".

The produced cetane improver composition would have the general following structure:

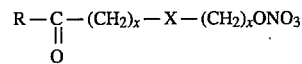

where

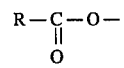

is the fatty acids, crude tall oil mixture group

Nitration can be accomplished by using nitric-sulfuric acid mixtures, as disclosed in U.S. Pat. No. 4,406,655, or by using a nitric acid/acetic anhydride mixture as described by E. S. Lane in J. Chem. Soc. Part 2, 1172 (1953)

More particularly, tall oil fatty alcohol nitrate esters can be obtained by the hydrogenation of tall oil fatty acids to the alcohols using rhenium heptoxide catalyst as in the procedure disclosed by Broadbent et al, J. Org. Chem 24, 1847, 1959 or by the hydrogenation of the corresponding ester using copper chromate catalyst or the like or by hydrogenation with Raney-Nickel Catalyst followed by Bouveault-Blanc method (sodium in refluxing ethanol) followed by nitration of the resulting alcohols.

The tall oil fatty acid esters include the $C_1$ to $C_{10}$ esters, preferably the $C_1$ to $C_8$ esters, including, by way of example only, methyl, ethyl, propyl, isopropyl, n-butyl, sec butyl, tert butyl, amyl, hexyl, cyclohexyl, heptyl, octyl.

Fuel compositions containing from 0.01 to about 2 wt %, preferably 0.01 to about 1 wt %, more preferably 0.05 to about 0.6 wt % of fatty alcohol nitrate ester exhibit improvements in the cetane rating of the fuel as compared to that exhibited by the same fuel in the absence of such additive. Cetane number of a diesel fuel increases on the order of 0.5 to 6 or more depending on the quantity of additives used.

EXAMPLES

General Nitration Procedures

In all of the following examples the following procedure was employed to prepare the nitrate samples reported and evaluated.

Charge 1 mole of acetic anhydride to a 1L round bottom flask and cool to 5°–10° C. while agitating with mechanical stirrer. Charge 1 mole of fuming nitric acid to an addition funnel and add dropwise to the acetic anhydride. Control the exotherm to less than 12° C. by regulating the addition rate. After all of the fuming nitric acid is added, allow to stir for 30 minutes. Charge 0.75 mole of alcohols or fatty acids to the addition funnel and add dropwise to the reaction flask as before maintaining temperature less than 12° C. After all the alcohols/fatty acids were added allow the temperature to rise to room temperature and continue stirring for 8 hours. Stop agitation and transfer contents to separatory funnel for washing. Then charge equal amount by weight of saturated brine solution and shake. After separation, drain the water layer. Repeat the washing procedure until the pH is about 4. Analyze product layer for water by Karl-Fischer and dry over sodium sulphate if needed. Filter to get final product.

Comparative Example 1

A sample of tall oil fatty acids was nitrated in accordance with the general nitration procedure recited above. The nitrated tall oil fatty acids is a viscous orange liquid slightly soluble in diesel (up to about 0.05 wt %) but very soluble in aromatic hydrocarbons. The following results show that the effectiveness of the nitrated tall oil fatty acids is limited by its solubility in diesel fuel and is not per se very high.

|  | Treat rate, wt % | Cetane Number (D-613) |
| --- | --- | --- |
| Base diesel (MAP-2355) | 0 | 40.4 |
| Nitrated tall oil fatty acids | 0.02 | 41.6 |
| Nitrated tall oil fatty acids | 0.04 | 42.7 |
| Nitrated tall oil fatty acids | 0.06 | 43.7 |
| Nitrated tall oil fatty acids | 0.08 | 40.6 |

Comparative Example 2

This example describes the preparation of tall oil fatty acid glycols. The olefinic double bond of the tall oil fatty acids were oxidized to produce the glycols. The glycols were then nitrated to give an orange waxy oil.
Preparation of the Tall Oil Fatty Acid Glycols Eighty-four milliliters (84 ml) of 30% hydrogen peroxide (0.81 mole) is added to 352 ml of 90% formic acid (8.0 moles) in a 1 L three-necked round bottom flask equipped with a thermometer, a magnetic bar and a condenser. Tall oil (80.0 g., 0.29 mole) is added slowly from a dropping funnel over a period of 30 minutes while the temperature of the reaction mixture is maintained below 40° C. by cooling with an ice-bath and controlling the rate of addition. The reaction mixture is kept at 40° C. for 1 hour after all the tall oil has been added, and then it is allowed to stand overnight with stirring at room temperature.

The hydroxy acylated product is separated from the water by extraction with ethyl acetate. The organic layer is washed several times with aqueous sodium chloride/sodium sulphite solution and then with water to remove residual peroxide. The ethyl acetate fraction is then dried over magnesium sulphate anhydrous, filtered and the solvent removed under reduced pressure to yield a yellow viscous oil. An ice cold solution of 46.8 g sodium hydroxide in 88 ml water is added in small portions to the viscous mixture with care so that the temperature does not exceed 45° C. The alkaline solution is warmed to 45° C., and equal volume (150 ml) or more of ethyl acetate is added. A solution of 160 ml concentrated hydrochloric acid in 400 ml water is added to the flask with stirring. The aqueous fraction is extracted once with 150 ml ethyl acetate. The combined ethyl acetate fractions is then washed with water until neutrality of the washings. The organic phase is dried over sodium sulphate anhydrous, filtered, and the solvent removed under reduced pressure to yield 75.6 g (about 80.0% theoretical yield) of an orange viscous oil which solidifies at room temperature.
Preparation of the Tall Oil Fatty Acid Glycol Nitrate Esters The general nitration procedure recited above was used to prepare the product. However, 3 moles of fuming nitric acid and 3 moles of acetic anhydride to 0.75 mole of glycols were used.

The nitrated Fatty Acid Glycols are polar and were found very slightly soluble in diesel fuel. Only up to about 0.05 wt % of product dissolved in the diesel fuel. The following results show its relatively poor effectiveness to increase cetane number.

|  | Treat rate, wt % | Cetane Number (D-613) |
| --- | --- | --- |
| Base diesel (MAP-2355) | 0 | 40.4 |
| Nitrated tall oil fatty acid glycols | 0.02 | 41.6 |
| Nitrated tall oil fatty acid glycols | 0.05 | 42.3 |
| Nitrated tall oil fatty acid glycols | 0.06 | 41.6 |

EXAMPLE 1

This example describes an embodiment of the present invention, tall oil fatty alcohol nitrate esters cetane improvement additives and a method for their preparation.
Preparation of the Tall Oil Fatty Acid Methyl Ester To a 2 L round bottom flask equipped with a reflux condenser, a magnetic bar and a drying tube, was placed 361.4 g (1.3 mole based on linoleic acid) of tall oil fatty acids. 780 ml of dry methanol and 78 ml of concentrated sulfuric acid. The mixture was stirred with a magnetic stirrer and refluxed for 25 hours. The cooled mixture was transferred into a 3 liter separatory funnel. About 500 ml of water was added to the mixture followed by about 1000 ml of ether. The aqueous layer was separated and washed with 300 ml ether.

The combined ether fractions were washed with 4×500 ml portion of 0.4% (0.1N) sodium hydroxide solution. The pH of the washings was 10–11. The ether fraction was then washed with water until neutral to the pH paper and then dried over anhydrous sodium sulphate. The ether was removed under reduced pressure to yield 322.4 g of esters (about 85.0% yield). The esters mixture is liquid at room temperature with a golden brown color.

Hydrogenation of Tall Oil Fatty Acids Methyl Ester

To a 1L high pressure autoclave equipped with a rupture disk (1400 psi) and check valves, is added 40 g Raney nickel catalyst (W2) dispersed into 260 ml isopropanol. The tall oil fatty acids methyl ester (200 g) is then added to the catalyst slurry. The autoclave is purged with nitrogen to exclude air then purged 2 to 3 times with hydrogen. The autoclave is pressurized at 200 psi with hydrogen and the temperature adjusted to about 150° C. The pressure is continuously set at 400 psi as long as the product is adsorbing hydrogen. The hydrogenation is continued until the mixture did not adsorb hydrogen anymore. The autoclave is cooled and depressurized. When cooled, the reaction mixture is filtered through Whatman filter paper using slight vacuum. The catalyst is then transferred to a jar covered with water. The filtered solution is extracted with ether and washed with water to remove isopropanol. The organic fraction is dried over anhydrous sodium sulphate, filtered and the solvent removed under reduced pressure to yield quantitative amount of hydrogenated tall oil fatty acids methyl esters having the consistency of margarine.

Preparation of the Tall Oil Fatty Alcohols

A 5 L three-necked round bottom flask was equipped with a mechanical air stirrer, an addition funnel, a reflux condenser and a heating mantle. The top of the condenser was connected to a tygon tube hooked up to a gas bubbler filled with paraffinic oil. In the flask were placed 23.8 g (1.04 mole) of sodium (finely divided) in 60 ml of dry toluene. At about 60° C., there was added from the addition funnel, a solution of 50.0 g (0.17 mole) of hydrogenated tall oil fatty acid methyl ester in 50 ml of absolute ethanol, then 160 ml more ethanol was added as rapidly as possible without loss of material through the addition funnel. The time required for the addition of the ester solution and alcohol was 3–4 minutes. When the reaction has subsided, the flask was heated to reflux for 1.5 hours until the sodium has completely dissolved. The ethanol and toluene were then removed under reduced pressure at (40° C.). To the contents of the flask was added about 2×200 ml of warm water. The cooled solution was then transferred to a separatory funnel. About 400 ml of ether was then added. The aqueous layer was separated and washed 2 times with 200 ml of ether. The combined ether fractions were then washed with water until neutral to the pH paper. The ether phase was treated with activated charcoal and dried over sodium sulphate anhydrous, filtered and the ether removed under reduced pressure to yield 37.4 g of alcohols (~82.7% yield).

Preparation of the Tall Oil Fatty Alcohol Nitrate Esters

The same general nitrating procedure described above was used to prepare the tall oil fatty alcohol nitrate esters (TOFANE) from the alcohol described above.

The effectiveness of the tall oil fatty alcohol nitrate esters are presented in Table 1. The results are compared with docedyl nitrate and 2-ethylhexyl nitrate.

The data shows that relatively good cetane improver compositions can be obtained from inexpensive feedstock (tall oil) a by-product from the Pulp Mill industry.

TABLE 1

| CETANE IMPROVER EFFECTIVENESS (ASTM D613) | | | |
| --- | --- | --- | --- |
| Treat rate wt % | Isooctyl nitrate (2) | Cetane Increase (1) Dodecyl nitrate | TOFANE (3) |
| 0 | 0 | 0 | 0 |
| 0.03 | 2.8 | 2.4 | 0.5 (0.7) |
| 0.06 | 4.9 | 4.3 | — |
| 0.1 | — | 4.4 | 2.0 (2.7) |
| 0.2 | 7.0 | 6.4 | 3.2 (4.3) |
| 0.3 | 8.2 | 8.3 | 4.5 (6.0) |

(1) Single determination in diesel fuel with 40.4 CN.
(2) Also known as 2-ethylhexyl nitrate (Ethyl's D11-3)
(3) Number in brackets correspond to 100% TOFANE.

The 100% TOFANE performance is based on an extrapolation of performance of the actual TOFANE sample of known purity. GC/MS analysis and FTIR results indicated that there is about 25% of fatty acid esters (not nitrate esters) which have not been reduced to alcohols, thus not converted to desired fatty alcohols nitrate esters.

What is claimed is:

1. A cetane improver composition comprising a fatty alcohol nitrate ester.

2. The cetane improver composition of claim 1 wherein the fatty alcohol nitrate ester is a tall oil fatty alcohol nitrate ester.

3. The cetane improver composition of claim 1 wherein the fatty alcohol nitrate ester is the nitration production of tall oil fatty alcohols, vegetable oil fatty alcohols and mixtures thereof.

4. A diesel fuel or middle distillate fraction, excluding jet, of improved cetane number comprising a major amount of diesel fuel or middle distillate fraction and a minor amount of a fatty alcohol nitrate ester.

5. The diesel fuel or middle distillate fraction, excluding jet, of improved cetane number of claim 4 wherein the fatty alcohol nitrate ester is present in an amount in the range of 0.01 to about 2 wt %.

* * * * *